United States Patent [19]

Yamamoto et al.

[11] 4,029,798
[45] June 14, 1977

[54] ANALGETIC COMPOSITION

[75] Inventors: Hisao Yamamoto, Kobe; Toshiya Inukai, Sanda; Yoshihiko Koga, Minoo, all of Japan

[73] Assignee: Sumitomo Chemical Company, Limited, Osaka, Japan

[22] Filed: June 2, 1975

[21] Appl. No.: 582,757

[52] U.S. Cl. .................................. 424/260; 424/274
[51] Int. Cl.² ................ A61K 31/485; A61K 31/40
[58] Field of Search ............................ 424/260, 274

[56] References Cited

UNITED STATES PATENTS

| | | | |
|---|---|---|---|
| 3,161,654 | 12/1964 | Shen | 260/326.12 A |
| 3,250,678 | 5/1966 | Archer | 424/267 |
| 3,551,446 | 12/1970 | Yamamoto et al. | 260/326.13 A |
| 3,576,800 | 4/1971 | Yamamoto et al. | 260/287 R |
| 3,812,112 | 5/1974 | Kemura et al. | 424/274 |
| 3,833,595 | 9/1974 | Atsumi et al. | 260/293.54 |

OTHER PUBLICATIONS

The Merck Index, 8th Ed., p. 794, Published by Merck & Co. Inc., Rahway, N. J. (1968).

Primary Examiner—Donald B. Moyer
Attorney, Agent, or Firm—Stevens, Davis, Miller & Mosher

[57] ABSTRACT

An alalgetic composition which comprises, as an active ingredient, a therapeutically effective amount of a synergistic mixture of an indole-3-acetic acid derivative of the formula,

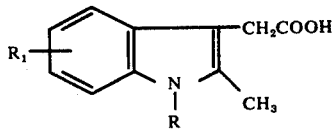

wherein R is a halobenzoyl, piperonyloyl or cinnamoyl group and $R_1$ is a 5-methoxy or 5,6-methylenedioxy group; and a narcotic or anti-narcotic analgesic selected from the group consisting of a compound of the formula,

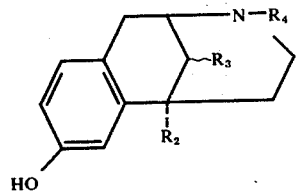

wherein $R_2$ and $R_3$ are each a $C_1 - C_3$ alkyl group and $R_4$ is a 4-(4-fluorophenyl)-4-oxobutyl, cyclopropylmethyl or 3-methyl-2-butenyl group; a compound of the formula,

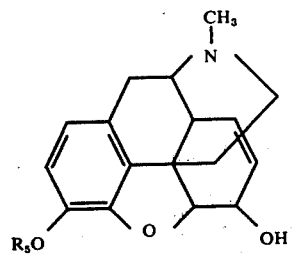

wherein $R_5$ is a hydrogen atom or a $C_1 - C_3$ alkyl group; a compound of the formula,

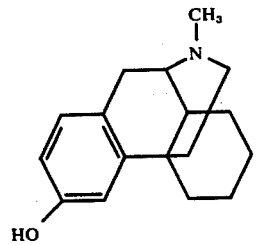

and a compound of the formula,

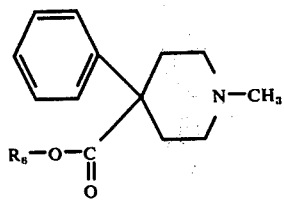

wherein $R_6$ is a $C_1 - C_3$ alkyl group; and a pharmaceutically acceptable carrier or diluent and its preparation and a method of obtaining analgesia which comprises administering the same to a patient.

28 Claims, No Drawings

ANALGETIC COMPOSITION

This invention relates to an analgetic composition which brings about highly synergistic efficacy and to a method of obtaining powerful analgesia. More particularly, this invention relates to an analgetic composition which comprises, as an active ingredient, a therapeutically effective amount of a synergistic mixture of an indole-3-acetic acid derivative and a narcotic or anti-narcotic analgesic and a pharmaceutically acceptable carrier or diluent, and its preparation and to a method of obtaining analgesia which comprises administering the same to a patient.

As the result of the study on the pharmacological properties of these compounds, surprisingly it has been found that the combination of the indole-3-acetic acid derivative and the narcotic or anti-narcotic analgesic brings about highly synergistic analgetic efficiency.

Although each of these compounds displays an analgetic activity, the combination of said indole-3-acetic acid derivative and said narcotic or anti-narcotic analgesic provides a remarkably higher analgetic activity than the sum of the activities displayed by each of the compounds. This synergistic efficacy obtained according to the present invention gives many advantages in the practical usage of these compounds, for instance, it allows the employment of very low doses of these compounds to obtain analgesia, and hence it diminishes significantly troublesome side effects caused by the single administration of the abovementioned compounds for obtaining sufficient analgesia, when it is required to use much larger dosages compared with the use of the synergistic mixture of the present invention. Furthermore, the administration of the synergistic mixture of the present invention gives most strong analgesia which can not be achieved by the administration of any one of these compounds.

Accordingly, the present invention provides a new type of analgetic composition which comprises an analgetically effective amount of a synergistic mixture of an indole-3-acetic acid derivative of the formula,

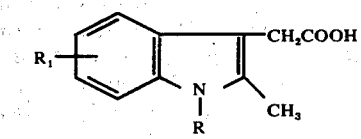

wherein R is a halobenzoyl, piperonyloyl or cinnamoyl group and $R_1$ is a 5-methoxy or 5,6-methylenedioxy group; and a narcotic or anti-narcotic analgesic selected from the group consisting of a compound of the formula,

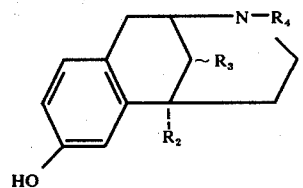

wherein $R_2$ and $R_3$ are each a $C_1 - C_3$ alkyl group and $R_4$ is a 4-(4-fluorophenyl)-4-oxobutyl, cyclopropylmethyl or 3-methyl-2-butenyl group; a compound of the formula,

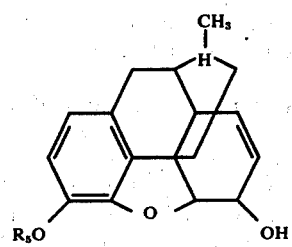

wherein $R_5$ is a hydrogen atom or a $C_1 - C_3$ alkyl group; a compound of the formula,

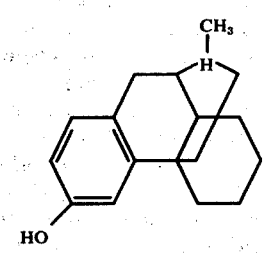

and a compound of the formula,

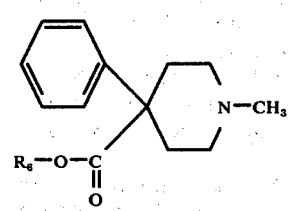

wherein $R_6$ is a $C_1 - C_3$ alkyl group; and a pharmaceutically acceptable carrier or diluent. This invention further provides a method of obtaining improved analgesia which comprises administering the same to a patient and a process for preparing the same which comprises admixing the indole-3-acetic acid derivative and th narcotic or anti-narcotic analgesic together with a pharmaceutically acceptable carrier or diluent.

The term used herein "halobenzoyl" means benzoyl substituted with a halogen atom such as a chlorine or fluorine atom. The term "$C_1- C_3$ alkyl" means alkyl having one to three carbon atoms such as methyl, ethyl, n-propyl or isopropyl.

The indole-3-acetic acid derivative used as an active ingredient in the composition of the present invention is well-known to have an anti-inflammatory, hydpothermic and analgetic activity. (J. Am. Chem. Soc., 85, 488 (1963); U.S. Pat. Nos. 3,576,800; 3,551,446; 3,812,112.)

The narcotic or anti-narcotic analgesic employed as another active ingredient is also known to have an analgetic activity. (U.S. Pat. No. 3,833,595; J. Med. Chem. 7, 123 (1964); "Medicinal Chemistry" (George de Stevens, Ed.) Vol. 5, Analgeticis, Academic Press, New York and London (1965))

According to the present invention, the improved analgesia can be obtained by administering the synergistic mixture of said indole-3-acetic acid derivative and said narcotic or anti-narcotic analgesic to mammals.

For this purpose, said mixture of an indole-3-acetic acid derivative and said narcotic or anti-narcotic analgesic are brought into a suitable dosage unit form (e.g., tablets, powders, suspensions, solutions, suppositories, etc.) together with a conventional pharmaceutical carrier or diluent using the conventional procedures in the art.

With respect to the weight ratio of said indole-3-acetic acid derivative to said narcotic or anti-narcotic analgesic, a desirable ratio, from the practical point of view, is 3 : 97 to 90 : 10, preferably 10 : 90 to 75 : 25 and more preferably 25 : 75 to 65 : 35. However, even beyond these ranges, some synergistic effect will be observed.

The analgetic composition of the present invention may contain about 0.05 to 90% by weight of the synergistic mixture as an active ingredient.

Among the indole-3-acetic acid derivatives, preferred examples include 1-(4-chlorobenzoyl)-2-methyl-5-methoxyindole-3-acetic acid, 1-cinnamoyl-2-methyl- 5-methoxyindole-3-acetic acid, 1-piperonyloyl-2-methyl-5-methoxyindole-3-acetic acid, 1-cinnamoyl-2-methyl-5,6-methylenedioxyindole-3-acetic acid, 1-(4-fluorobenzoyl)-2-methyl-5,6-methylenedioxyindole-3-acetic acid and 1-(4-chlorobenzoyl)-2-methyl-5,6-methylenedioxyindole-3-acetic acid.

Among the narcotic or anti-narcotic analgesics, 3-(4-(4-fluorophenyl)-4-oxobutyl)-1,2,3,4,5,6-hexahydro-6,11-dimethyl-2,6-methano-3-benzazocin-8-ol, 1,2,3,4,5,6-hexahydro-6,11-dimethyl-3-(3-methyl-2-butenyl)-2,6-methano-3-benzazocin-8-ol, 3-cyclopropyl-methyl-1,2,3,4,5,6-hexahydro-6,11-dimethyl-2,6-methano-3-benzazocin-8-ol, morphine and ethyl 1-methyl-4-phenylpiperidine-4-carboxylate are preferred.

Particularly, the administration of the combination of 1-(4-chlorobenzoyl)-2-methyl-5-methoxyindole-3-acetic acid and the above specified analgesic and of the combination of 3-(4-(4-fluorophenyl)-4-oxobutyl-1,2,3,4,5,6-hexahydro-6,11-dimethyl-2,6-methano-3-benzazocin-8-ol and the above specified indole-3-acetic acid derivative provide an excelent analgesia.

The synergistic composition of the present invention can be administered orally, rectally or parenterally in total daily doses of the active ingredient ranging from about 0.2 to 200 mg/man, more preferably 0.5 to 100 mg/man. To this purpose, these mixture may be formulated, for example, to suitable pharmaceutical compositions such as tablets, capsules, solutions, suppositories, powders or suspensions.

The compositions for oral administration may include carriers or excipients coventionally used in the ordinary pharmaceutical art. Thus, for example, suitable tabletting adjuvants include calcium carbonate, calcium phosphate, corn starch, potato starch, sucrose, lactose, talc, magnesium stearate and gum acacia.

For parenteral administration, the carrier may be sterile, parenterally acceptable liquid such as sterile water, essential oil such as peanut oil, corn oil or non-aqueous solvent such as polyethlene glycol or polypropylene glycol.

Compositions for rectal administration may take the form of suppositories and the carrier comprises a conventional suppository base such as polyethylene glycol, lanolin or coconut butter.

The synergistic effect of the present invention will be illustrated by the following examples, but the present invention is not limited to those.

EXAMPLE 1

1-(4-Chlorobenzoyl)-2-methyl-5-methoxyindole-3-acetic acid (I) and 3-(4-(4-fluorophenyl)-4-oxobutyl)-1,2,3,4,5,6-hexahydro-6,11-dimethyl-2,6-methano-3-benzazocin-8-ol (II) were individually formulated by use of tragacanth into 0.01%, 0.03%, 0.05%, 0.07%, 0.1%, 0.3%, 0.5%, 0.7% and 1.0% suspensions.

In the same manner mentioned above, there were formulated 0.05%, 0.1% and 0.2% tragacanth suspensions of individual mixtures comprising the compound (I) and the compound (II) in such ratios as 0.1 : 9.9, 0.3 : 9.7, 0.7 : 9.3, 1.0 : 9.0, 1.7 : 8.3, 2.5 : 7.5, 3.5 : 6.5, 4.5 : 5.5, 5.0 : 5.0, 5.5 : 4.5, 6.5 : 3.5, 7.5 : 2.5, 8.5 : 1.5, 9.0 : 1.0 and 9.9 : 0.1.

On the other hand, male mice of dd-strain weighing from 20 to 25 g were prepared for the evaluation of analgetic activity. Each sample was given to animals in a volume of 0.1 ml per 10 g body weight. One hour after test drugs were administered orally to the animals, 0.1 ml of 0.6% (v/v) acetic acid per 10 g body weight of the animal was injected intraperitoneally. Then, nociceptive reaction of the animal such as writhing or stretching of the abdomen were observed carefully. Suppression of these reactions by the test drug was regarded as positive effect and analgetic activity of the drug was evaluated. Analgetic activity was expressed as percent of animals which showed analgesia in total animals used. The results were as set forth in Table 1, and thus the two compounds obviously showed significant synergistic effects.

Table 1

| Compound (I) | | Compound (II) | | Mixture of compound (I) and compound (II) | | |
| --- | --- | --- | --- | --- | --- | --- |
| Concentration (%) | Analgetic Activity | Concentration (%) | Analgetic Activity | Mixing ratio of compound (I): compound (II) | Concentration (%) | Analgetic Activity |
| 0.01 | 0 | 0.01 | 0 | 0.1 : 9.9 | 0.05 | 21 |
| 0.03 | 0 | 0.03 | 0 | 0.3 : 9.7 | 0.05 | 44 |
| 0.05 | 0 | 0.05 | 0 | 0.7 : 9.3 | 0.05 | 53 |
| 0.07 | 0 | 0.07 | 4 | 1.0 : 9.0 | 0.05 | 64 |
| 0.1 | 2 | 0.1 | 11 | 1.7 : 8.3 | 0.05 | 67 |
| 0.3 | 9 | 0.3 | 37 | 2.5 : 7.5 | 0.05 | 79 |
| 0.5 | 21 | 0.5 | 61 | 3.5 : 6.5 | 0.05 | 86 |
| 0.7 | 44 | 0.7 | 83 | 4.5 : 5.5 | 0.05 | 90 |
| 1.0 | 68 | 1.0 | 100 | 5.0 : 5.0 | 0.05 | 98 |
| | | | | 5.5 : 4.5 | 0.05 | 96 |
| | | | | 6.5 : 3.5 | 0.05 | 82 |
| | | | | 7.5 : 2.5 | 0.05 | 66 |
| | | | | 8.5 : 1.5 | 0.05 | 52 |
| | | | | 9.0 : 1.0 | 0.05 | 47 |
| | | | | 9.9 : 0.1 | 0.05 | 19 |

Table 1-continued

| Mixture of Compound (I) and Compound (II) | | | | |
|---|---|---|---|---|
| Mixing ratio of compound (I): compound (II) | Concentration (%) | Analgetic Activity | Concentration (%) | Analgetic Activity |
| 0.1 : 9.9 | 0.1 | 30 | 0.2 | 52 |
| 0.3 : 9.7 | 0.1 | 48 | 0.2 | 73 |
| 0.7 : 9.3 | 0.1 | 62 | 0.2 | 84 |
| 1.0 : 9.0 | 0.1 | 71 | 0.2 | 88 |
| 1.7 : 8.3 | 0.1 | 74 | 0.2 | 96 |
| 2.5 : 7.5 | 0.1 | 86 | 0.2 | 98 |
| 3.5 : 6.5 | 0.1 | 90 | 0.2 | 100 |
| 4.5 : 5.5 | 0.1 | 98 | 0.2 | 100 |
| 5.0 : 5.0 | 0.1 | 100 | 0.2 | 100 |
| 5.5 : 4.5 | 0.1 | 100 | 0.2 | 100 |
| 6.5 : 3.5 | 0.1 | 92 | 0.2 | 100 |
| 7.5 : 2.5 | 0.1 | 75 | 0.2 | 94 |
| 8.5 : 1.5 | 0.1 | 62 | 0.2 | 88 |
| 9.0 : 1.0 | 0.1 | 37 | 0.2 | 64 |
| 9.9 : 0.1 | 0.1 | 34 | 0.2 | 40 |

As shown in Table 1, the mixture of compound I and compound II showed a powerful analygetic effect. The efficacy of this mixture was significantly greater than that of the ingredient, compound I or compound II administered separately.

Compound I at lower concentration than 0.07% and compound II at lower concentration than 0.05% did not show any analgetic effect. When these compounds were given together, clear synergism was observed.

In 0.05% suspension of the mixture of mixing ratio (compound I: compound II) 5.0 : 5.0, for example, 0.025% of compound I and 0.025% of compound II were contained. At the concentration of 0.025%, neither compound I nor compound II, by itself, showed significant analgesia. However, the mixture of these compounds showed potent analgetic activity, 98%. When the ingredient was given separately, such analgetic effect was produced by compound I at a concentration as high as 1.0% or more, or by compound II at a concentration as high as nearly 1.0%.

Maximum analgetic effect of the mixture at 0.05% of concentration was obtained at the mixing ratio 5.0 : 5.0, but te synergism was observed in the wide range of mixing ratio.

At the mixing ratio from 0.3 : 9.7 to 9.0 : 1.0, the analgetic activites of the mixtures were more than 44% which was apparently greater than that expected for the additive effect of compounds I and II. Because the concentration of compound I or compound II in the mixtures of various mixing ratio could not exceed 0.05%, which was by itself an ineffective dose for analgesia. At the mixing ratio from 1.0 : 9.0 to 7.5 : 2.5, the analgetic activities of the mixtures were more than 64%, and at the ratio from 2.5 : 7.5 to 6.5 : 3.5, the activities of the mixtures were more than 79%.

In other words, we can considerably reduce the dose requisite for sufficient analgesia by use of the combination of compound I and compound II. Consequently troublesome side effects of the drugs, if any, would be reduced.

EXAMPLE 2

The compound (I) and 1,2,3,4,5,6-hexahydro-6,11-dimethyl-3-(3-methyl-2-butenyl)-2,6-methano-3-benzazocin-8-ol (III) were used in accordance with the manner similar to that of Example 1.

The results obtained were as set forth in Table 2.

EXAMPLE 3

The compound (I) and morphine (IV) were used as described in Example 1 and the results obtained were shown in Table 3.

EXAMPLE 4

The compound (I) and codeine (V) were used as described in Example 1 and the results obtained were shown in Table 4.

EXAMPLE 5

The compound (I) and 3-hydroxy-N-methyl-morphinan (VI) were used as described in Example 1 and the results obtained were shown in Table 5.

EXAMPLE 6

The compound (I) and ethyl 1-methyl-4-phenyl-piperidine-4-carboxylate (VII) were used as described in Example 1 and the results obtained were shown in Table 6.

EXAMPLE 7

The compound (I) and 3-cyclopropylmethyl-1,2,3,4,5,6-hexahydro-6,11-dimethyl-2,6-methano-3-benzazocin-8ol (VIII) were used as described in Example 1 and the results obtained were shown in Table 7.

EXAMPLE 8

1-Cinnamoyl-2-methyl-5-methoxyindole-3-acetic acid (IX) and the compound (II) were administered in accordance with the same manner as described in Example 1. The results obtained were shown in Table 8.

EXAMPLE 9

1-Piperonyloyl-2-methyl-5-methoxyindole-3-acetic acid (X) and the compound (II) were used as described in Example 1. The results obtained were shown in Table 9.

EXAMPLE 10

1-Cinnamoyl-2-methyl-5,6-methylenedioxyindole-3-acetic acid (XI) and the compound (II) were administered to the animals as described in Example 1. The results were given in Table 10.

EXAMPLE 11

1-(4-Fluorobenzoyl)-2-methyl-5,6-methylenedioxyindole-3-acetic acid (XII) and the compound (II)

were used as described in Example 1 and the results obtained were shown in Table 11.

EXAMPLE 12

1-(4-Chlorobenzoyl)-2-methyl-5,6-methylenedioxyindole-3-acetic acid (XIII) and the compound (II) were used as described in Example 1. The results were given in Table 12.

Table 2

| Compound (I) | | Compound (III) | | Mixture of compound (I) and compound (III) | | |
|---|---|---|---|---|---|---|
| Concentration (%) | Analgetic Activity | Concentration (%) | Analgetic Activity | Mixing ratio of compound (I): compound (III) | Concentration (%) | Analgetic Activity |
| 0.01 | 0 | 0.01 | 0 | 0.1 : 9.9 | 0.3 | 10 |
| 0.03 | 0 | 0.03 | 0 | 0.3 : 9.7 | 0.3 | 24 |
| 0.05 | 0 | 0.05 | 0 | 1.0 : 9.0 | 0.3 | 44 |
| 0.07 | 0 | 0.07 | 0 | 1.7 : 8.3 | 0.3 | 52 |
| 0.1 | 2 | 0.1 | 7 | 2.5 : 7.5 | 0.3 | 65 |
| 0.3 | 6 | 0.3 | 11 | 3.5 : 6.5 | 0.3 | 71 |
| 0.5 | 20 | 0.5 | 14 | 4.5 : 5.5 | 0.3 | 75 |
| 0.7 | 46 | 0.7 | 36 | 5.0 : 5.0 | 0.3 | 83 |
| 1.0 | 72 | 1.0 | 63 | 5.5 : 4.5 | 0.3 | 73 |
| | | | | 6.5 : 3.5 | 0.3 | 67 |
| | | | | 7.5 : 2.5 | 0.3 | 42 |
| | | | | 8.5 : 1.5 | 0.3 | 23 |
| | | | | 9.0 : 1.0 | 0.3 | 9 |
| | | | | 9.9 : 0.1 | 0.3 | 0 |

Table 3

| Compound (I) | | Compound IV | | Mixture of compound (I) and compound (IV) | | |
|---|---|---|---|---|---|---|
| Concentration (%) | Analgetic Activity | Concentration (%) | Analgetic Activity | Mixing ratio of compound (I): compound (IV) | Concentration (%) | Analgetic Activity |
| 0.001 | 0 | 0.005 | 0 | 0.1 : 9.9 | 0.03 | 4 |
| 0.005 | 0 | 0.01 | 0 | 0.3 : 9.7 | 0.03 | 24 |
| 0.01 | 0 | 0.03 | 6 | 0.7 : 9.3 | 0.03 | 47 |
| 0.03 | 0 | 0.05 | 12 | 1.0 : 9.0 | 0.03 | 58 |
| 0.05 | 0 | 0.07 | 38 | 1.7 : 8.3 | 0.03 | 62 |
| 0.07 | 0 | 0.1 | 54 | 2.5 : 7.5 | 0.03 | 63 |
| 0.1 | 4 | 0.3 | 82 | 3.5 : 6.5 | 0.03 | 77 |
| 0.3 | 12 | 0.5 | 88 | 4.5 : 5.5 | | |
| 0.5 | 22 | 0.7 | 100 | 5.0 : 5.0 | 0.03 | 97 |
| 0.7 | 48 | 1.0 | 100 | 5.5 : 4.5 | 0.03 | 83 |
| 1.0 | 66 | | | 6.5 : 3.5 | 0.03 | 69 |
| | | | | 7.5 : 2.5 | 0.03 | 55 |
| | | | | 8.5 : 1.5 | 0.03 | 42 |
| | | | | 9.0 : 1.0 | 0.03 | 11 |
| | | | | 9.9 : 0.1 | 0.03 | 0 |

Table 4

| Compound (I) | | Compound (V) | | Mixture of compound (I) and compound (V) | | |
|---|---|---|---|---|---|---|
| Concentration (%) | Analgetic Activity | Concentration (%) | Analgetic Activity | Mixing ratio of compound (I): compound (V) | Concentration (%) | Analgetic Activity |
| 0.01 | 0 | 0.01 | 0 | 0.1 : 9.9 | 0.1 | 8 |
| 0.03 | 0 | 0.03 | 0 | 0.3 : 9.7 | 0.1 | 16 |
| 0.05 | 0 | 0.05 | 0 | 1.0 : 9.0 | 0.1 | 28 |
| 0.07 | 0 | 0.07 | 0 | 1.7 : 8.3 | 0.1 | 32 |
| 0.1 | 0 | 0.1 | 8 | 2.5 : 7.5 | 0.1 | 44 |
| 0.3 | 12 | 0.3 | 24 | 3.5 : 6.5 | 0.1 | 61 |
| 0.5 | 24 | 0.5 | 52 | 4.5 : 5.5 | 0.1 | 77 |
| 0.7 | 42 | 0.7 | 86 | 5.0 : 5.0 | 0.1 | 83 |
| 1.0 | 70 | 1.0 | 98 | 5.5 : 4.5 | 0.1 | 74 |
| | | | | 6.5 : 3.5 | 0.1 | 54 |
| | | | | 7.5 : 2.5 | 0.1 | 46 |
| | | | | 8.5 : 1.5 | 0.1 | 38 |
| | | | | 9.0 : 1.0 | 0.1 | 13 |
| | | | | 9.9 : 0.1 | 0.1 | 0 |

Table 5

| Compound (I) | | Compound (VI) | | Mixture of compound (I) and compound (VI) | | |
|---|---|---|---|---|---|---|
| Concentration (%) | Analgetic Activity | Concentration (%) | Analgetic Activity | Mixing ratio of compound (I): compound (VI) | Concentration (%) | Analgetic Activity |
| 0.001 | 0 | 0.005 | 0 | 0.1 : 9.9 | 0.03 | 18 |
| 0.005 | 0 | 0.01 | 0 | 0.3 : 9.7 | 0.03 | 42 |
| 0.01 | 0 | 0.03 | 14 | 0.7 : 9.3 | 0.03 | 46 |
| 0.03 | 0 | 0.05 | 28 | 1.0 : 9.0 | 0.03 | 54 |
| 0.05 | 0 | 0.07 | 36 | 1.7 : 8.3 | 0.03 | 71 |
| 0.07 | 0 | 0.1 | 42 | 2.5 : 7.5 | 0.03 | 76 |
| 0.1 | 2 | 0.3 | 64 | 3.5 : 6.5 | 0.03 | 83 |
| 0.3 | 10 | 0.5 | 72 | 4.5 : 5.5 | 0.03 | 98 |
| 0.5 | 30 | 0.7 | 86 | 5.0 : 5.0 | 0.03 | 100 |
| 0.7 | 42 | 1.0 | 90 | 5.5 : 4.5 | 0.03 | 84 |
| 1.0 | 72 | | | 6.5 : 3.5 | 0.03 | 82 |
| | | | | 7.5 : 2.5 | 0.03 | 69 |
| | | | | 8.5 : 1.5 | 0.03 | 47 |
| | | | | 9.0 : 1.0 | 0.03 | 21 |
| | | | | 9.9 : 0.1 | 0.03 | 0 |

Table 6

| Compound (I) | | Compound (VII) | | Mixture of compound (I) and compound (VII) | | |
|---|---|---|---|---|---|---|
| Concentration (%) | Analgetic Activity | Concentration (%) | Analgetic Activity | Mixing ratio of compound (I): compound (VII) | Concentration (%) | Analgetic Activity |
| 0.01 | 0 | 0.01 | 0 | 0.1 : 9.9 | 0.1 | 20 |
| 0.03 | 0 | 0.03 | 0 | 0.3 : 9.7 | 0.1 | 36 |
| 0.05 | 0 | 0.05 | 0 | 0.7 : 9.3 | 0.1 | 42 |
| 0.07 | 0 | 0.07 | 8 | 1.0 : 9.0 | 0.1 | 47 |
| 0.1 | 4 | 0.1 | 18 | 1.7 : 8.3 | 0.1 | 55 |
| 0.3 | 12 | 0.3 | 32 | 2.5 : 7.5 | 0.1 | 69 |
| 0.5 | 20 | 0.5 | 66 | 3.5 : 6.5 | 0.1 | 87 |
| 0.7 | 48 | 0.7 | 74 | 4.5 : 5.5 | 0.1 | 90 |
| 1.0 | 62 | 1.0 | 88 | 5.0 : 5.0 | 0.1 | 94 |
| | | | | 5.5 : 4.5 | 0.1 | 88 |
| | | | | 6.5 : 3.5 | 0.1 | 76 |
| | | | | 7.5 : 2.5 | 0.1 | 42 |
| | | | | 8.5 : 1.5 | 0.1 | 24 |
| | | | | 9.0 : 1.0 | 0.1 | 11 |
| | | | | 9.9 : 0.1 | 0.1 | 0 |

Table 7

| Compound (I) | | Compound (VIII) | | Mixture of compound (I) and compound (VIII) | | |
|---|---|---|---|---|---|---|
| Concentration (%) | Analgetic Activity | Concentration (%) | Analgetic Activity | Mixing ratio of compound (I): compound (VIII) | Concentration (%) | Analgetic Activity |
| 0.001 | 0 | 0.001 | 0 | 0.1 : 9.9 | 0.005 | 10 |
| 0.005 | 0 | 0.003 | 4 | 0.3 : 9.7 | 0.005 | 22 |
| 0.01 | 0 | 0.005 | 11 | 0.7 : 9.3 | 0.005 | 31 |
| 0.03 | 0 | 0.01 | 27 | 1.0 : 9.0 | 0.005 | 35 |
| 0.05 | 0 | 0.03 | 48 | 1.7 : 8.3 | 0.005 | 42 |
| 0.07 | 0 | 0.05 | 69 | 2.5 : 7.5 | 0.005 | 44 |
| 0.1 | 4 | 0.07 | 88 | 3.5 : 6.5 | 0.005 | 51 |
| 0.3 | 10 | 0.1 | 92 | 4.5 : 5.5 | 0.005 | 67 |
| 0.5 | 14 | 0.3 | 100 | 5.0 : 5.0 | 0.005 | 72 |
| 0.7 | 38 | 0.5 | 100 | 5.5 : 4.5 | 0.005 | 63 |
| 1.0 | 62 | | 100 | 6.5 : 3.5 | 0.005 | 55 |
| | | | | 7.5 : 2.5 | 0.005 | 21 |
| | | | | 8.5 : 1.5 | 0.005 | 13 |
| | | | | 9.0 : 1.0 | 0.005 | 7 |
| | | | | 9.9 : 0.1 | 0.005 | 0 |

Table 8

| Compound (IX) | | Compound (II) | | Mixture of compound (IX) and compound (II) | | |
|---|---|---|---|---|---|---|
| Concentration (%) | Analgetic Activity | Concentration (%) | Analgetic Activity | Mixing ratio of compound (IX): compound (II) | Concentration (%) | Analgetic Activity |
| 0.01 | 0 | 0.01 | 0 | 0.1 : 9.9 | 0.1 | 15 |
| 0.05 | 0 | 0.03 | 0 | 0.3 : 9.7 | 0.1 | 27 |
| 0.1 | 0 | 0.05 | 0 | 0.7 : 9.3 | 0.1 | 33 |
| 0.5 | 10 | 0.07 | 6 | 1.0 : 9.0 | 0.1 | 41 |
| 0.7 | 22 | 0.1 | 13 | 1.7 : 8.3 | 0.1 | 46 |
| 1.0 | 41 | 0.3 | 42 | 2.5 : 7.5 | 0.1 | 53 |

Table 8-continued

| Compound (IX) | | Compound (II) | | Mixture of compound (IX) and compound (II) | | |
|---|---|---|---|---|---|---|
| Concentration (%) | Analgetic Activity | Concentration (%) | Analgetic Activity | Mixing ratio of compound (IX): compound (II) | Concentration (%) | Analgetic Activity |
| 3.0 | 64 | 0.5 | 66 | 3.5 : 6.5 | 0.1 | 59 |
| 5.0 | 72 | 0.7 | 78 | 4.5 : 5.5 | 0.1 | 64 |
| | | 1.0 | 100 | 5.0 : 5.0 | 0.1 | 78 |
| | | | | 5.5 : 4.5 | 0.1 | 59 |
| | | | | 6.5 : 3.5 | 0.1 | 36 |
| | | | | 7.5 : 2.5 | 0.1 | 14 |
| | | | | 8.5 : 1.5 | 0.1 | 11 |
| | | | | 9.0 : 1.0 | 0.1 | 7 |
| | | | | 9.9 : 0.1 | 0.1 | 0 |

Table 9

| Compound (X) | | Compound (II) | | Mixture of compound (X) and compound (II) | | |
|---|---|---|---|---|---|---|
| Concentration (%) | Analgetic Activity | Concentration (%) | Analgetic Activity | Mixing ratio of compound (X): compound (II) | Concentration (%) | Analgetic Activity |
| 0.01 | 0 | 0.01 | 0 | 0.1 : 9.9 | 0.1 | 11 |
| 0.05 | 0 | 0.03 | 0 | 0.3 : 9.7 | 0.1 | 24 |
| 0.1 | 0 | 0.05 | 0 | 0.7 : 9.3 | 0.1 | 29 |
| 0.5 | 13 | 0.07 | 4 | 1.0 : 9.0 | 0.1 | 45 |
| 0.7 | 28 | 0.1 | 11 | 1.7 : 8.3 | 0.1 | 45 |
| 1.0 | 55 | 0.3 | 39 | 2.5 : 7.5 | 0.1 | 53 |
| 3.0 | 73 | 0.5 | 58 | 3.5 : 6.5 | 0.1 | 67 |
| 5.0 | 94 | 0.7 | 69 | 4.5 : 5.5 | 0.1 | 71 |
| | | 1.0 | 100 | 5.0 : 5.0 | 0.1 | 84 |
| | | | | 5.5 : 4.5 | 0.1 | 68 |
| | | | | 6.5 : 3.5 | 0.1 | 38 |
| | | | | 7.5 : 2.5 | 0.1 | 19 |
| | | | | 8.5 : 1.5 | 0.1 | 10 |
| | | | | 9.0 : 1.0 | 0.1 | 4 |
| | | | | 9.9 : 0.1 | 0.1 | 0 |

Table 10

| Compound (XI) | | Compound (II) | | Mixture of compound (XI) and compound (II) | | |
|---|---|---|---|---|---|---|
| Concentration (%) | Analgetic Activity | Concentration (%) | Analgetic Activity | Mixing ratio of compound (XI): compound (II) | Concentration (%) | Analgetic Activity |
| 0.01 | 0 | 0.01 | 0 | 0.1 : 9.9 | 0.05 | 13 |
| 0.05 | 0 | 0.03 | 0 | 0.3 : 9.7 | 0.05 | 24 |
| 0.1 | 0 | 0.05 | 0 | 0.7 : 9.3 | 0.05 | 38 |
| 0.5 | 12 | 0.07 | 7 | 1.0 : 9.0 | 0.05 | 39 |
| 0.7 | 26 | 0.1 | 11 | 1.7 : 8.3 | 0.05 | 45 |
| 1.0 | 43 | 0.3 | 48 | 2.5 : 7.5 | 0.05 | 53 |
| 3.0 | 62 | 0.5 | 63 | 3.5 : 6.5 | 0.05 | 62 |
| 5.0 | 88 | 0.7 | 70 | 4.5 : 5.5 | 0.05 | 71 |
| | | 1.0 | 94 | 5.0 : 5.0 | 0.05 | 74 |
| | | | | 5.5 : 4.5 | 0.05 | 67 |
| | | | | 6.5 : 3.5 | 0.05 | 55 |
| | | | | 7.5 : 2.5 | 0.05 | 41 |
| | | | | 8.5 : 1.5 | 0.05 | 15 |
| | | | | 9.0 : 1.0 | 0.05 | 7 |
| | | | | 9.9 : 0.1 | 0.05 | 0 |

Table 11

| Compound (XII) | | Compound (II) | | Mixture of compound (XII) and compound (II) | | |
|---|---|---|---|---|---|---|
| Concentration (%) | Analgetic Activity | Concentration (%) | Analgetic Activity | Mixing ratio of compound (XII): compound (II) | Concentration (%) | Analgetic Activity |
| 0.01 | 0 | 0.01 | 0 | 0.1 : 9.9 | 0.1 | 14 |
| 0.05 | 0 | 0.03 | 0 | 0.3 : 9.7 | 0.1 | 27 |
| 0.1 | 0 | 0.05 | 0 | 0.7 : 9.3 | 0.1 | 27 |
| 0.5 | 0 | 0.07 | 9 | 1.0 : 9.0 | 0.1 | 30 |
| 0.7 | 17 | 0.1 | 18 | 1.7 : 8.3 | 0.1 | 33 |
| 1.0 | 36 | 0.3 | 44 | 2.5 : 7.5 | 0.1 | 40 |
| 3.0 | 45 | 0.5 | 63 | 3.5 : 6.5 | 0.1 | 51 |
| 5.0 | 59 | 0.7 | 72 | 4.5 : 5.5 | 0.1 | 54 |
| | | 1.0 | 100 | 5.0 : 5.0 | 0.1 | 63 |
| | | | | 5.5 : 4.5 | 0.1 | 52 |
| | | | | 6.5 : 3.5 | 0.1 | 36 |
| | | | | 7.5 : 2.5 | 0.1 | 25 |

Table 11-continued

| Compound (XII) | | Compound (II) | | Mixture of compound (XII) and compound (II) | | |
|---|---|---|---|---|---|---|
| Concentration (%) | Analgetic Activity | Concentration (%) | Analgetic Activity | Mixing ratio of compound (XII): compound (II) | Concentration (%) | Analgetic Activity |
| | | | | 8.5 : 1.5 | 0.1 | 21 |
| | | | | 9.0 : 1.0 | 0.1 | 8 |
| | | | | 9.9 : 0.1 | 0.1 | 0 |

Table 12

| Compound (XIII) | | Compound (II) | | Mixture of compound (XIII) and compound (II) | | |
|---|---|---|---|---|---|---|
| Concentration (%) | Analgetic Activity | Concentration (%) | Analgetic Activity | Mixing ratio of compound (XIII): compound (II) | Concentration (%) | Analgetic Activity |
| 0.01 | 0 | 0.01 | 0 | 0.1 : 9.9 | 0.1 | 19 |
| 0.05 | 0 | 0.03 | 0 | 0.3 : 9.7 | 0.1 | 25 |
| 0.1 | 0 | 0.05 | 0 | 0.7 : 9.3 | 0.1 | 34 |
| 0.5 | 0 | 0.07 | 7 | 1.0 : 9.0 | 0.1 | 37 |
| 0.7 | 13 | 0.1 | 18 | 1.7 : 8.3 | 0.1 | 38 |
| 1.0 | 39 | 0.3 | 49 | 2.5 : 7.5 | 0.1 | 43 |
| 3.0 | 51 | 0.5 | 55 | 3.5 : 6.5 | 0.1 | 55 |
| 5.0 | 65 | 0.7 | 81 | 4.5 : 5.5 | 0.1 | 60 |
| | | 1.0 | 100 | 5.0 : 5.0 | 0.1 | 68 |
| | | | | 5.5 : 4.5 | 0.1 | 65 |
| | | | | 6.5 : 3.5 | 0.1 | 51 |
| | | | | 7.5 : 2.5 | 0.1 | 27 |
| | | | | 8.5 : 1.5 | 0.1 | 11 |
| | | | | 9.0 : 1.0 | 0.1 | 8 |
| | | | | 9.9 : 0.1 | 0.1 | 0 |

Practical and presently preferred compositions of the present invention are shown in the following Examples. Modifications of the procedures shown in these Examples will be obvious to those skilled in the art and these Examples do not limit the scope of the invention.

EXAMPLE 13

| Tablets (1) | Each tablet |
|---|---|
| 1-(4-Chlorobenzoyl)-2-methyl-5-methoxyindole-3-acetic acid | 5 mg |
| 3-(4-(4-Fluorophenyl)-4-oxobutyl)-1,2,3,4,5,6-hexahydro-6,11-dimethyl-2,6-methano-3-benzazocin-8-ol | 5 mg |
| Lactose | 240 mg |
| Corn starch | 60 mg |
| Magnesium stearate | 5 mg |
| Polyvinyl acetate | 4 mg |
| Tablets (2) | Each tablet |
| 1-(4-Chlorobenzoyl)-2-methyl-5-methoxyindole-3-acetic acid | 10 mg |
| 1,2,3,4,5,6-Hexahydro-6,11-dimethyl-3-(3-methyl-2-butenyl)-2,6-methano-3-benzazocin-8-ol | 10 mg |
| Lactose | 240 mg |
| Corn starch | 60 mg |
| Magnesium stearate | 5 mg |
| Polyvinyl acetate | 4 mg |
| Tablets (3) | Each tablet |
| 1-(4-Chlorobenzoyl)-2-methyl-5-methoxyindole-3-acetic acid | 2.5 mg |
| Morphine | 2.5 mg |
| Lactose | 240 mg |
| Corn starch | 60 mg |
| Magnesium stearate | 5 mg |
| Polyvinyl acetate | 4 mg |

The active ingredients are admixed with an adequate amount of lactose and wetted with a suitable amount of polyvinyl acetate-ethanol solution. The resultant wet substance is formulated into granules. The granules are dried, admixed with a small amount of magnesium stearate and talc and compressed to tablets.

EXAMPLE 14

| Suppositories: | Each suppository |
|---|---|
| 1-(4-Chlorobenzoyl)-2-methyl-5-methoxyindole-3-acetic acid | 20 mg |
| 3-(4-(4-Fluorophenyl)-4-oxobutyl)-1,2,3,4,5,6-hexohydro-6,11-dimethyl-2,6-methano-3-benzazocin-8-ol | 20 mg |
| Polyethylene glycol 6000 | 1900 mg |
| Polyethylene glycol 400 | 50 mg |

The active ingredients are dissolved in a suitable amount of polyethylene glycol suppository base with gentle heating, and the solution is coated to suppositories in an adequate mold.

What is claimed is:

1. An analgetic composition which comprises, as an active ingredient, a therapeutically effective amount of a synergistic mixture of an indole-3-acetic acid derivative of the formula,

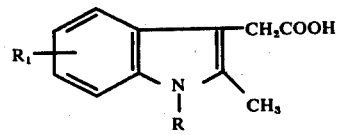

wherein R is a halobenzoyl, piperonyloyl, or cinnamoyl group and $R_1$ is a 5-methoxy or 5,6-methylenedioxy group; and an analgetic compound of the formula,

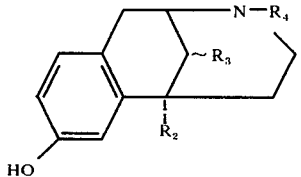

wherein $R_2$ and $R_3$ are each a $C_1 - C_3$ alkyl group and $R_4$ is a 4-(4-fluorophenyl)-4-oxobutyl, cyclopropylmethyl or 3-methyl-2-butenyl group and a pharmaceutically acceptable carrier or diluent, wherein the weight ratio of said indole-3-acetic acid derivative and said analgetic compound is from 3:97 to 90:10.

2. The analgetic composition of claim 1, wherein the weight ratio is from 10 : 90 to 75 : 25.

3. The analgetic composition of claim 1, wherein the weight ratio is from 25 : 75 to 65 : 35.

4. The analgetic composition of claim 1, wherein the synergistic mixture contains an indole-3-acetic acid derivative selected from the group consisting of 1-(4-chlorobenzoyl)-2-methyl-5-methoxyindole-3-acetic acid, 1-cinnamoyl-2-methyl-5-methoxyindole-3-acetic acid, 1-piperonyloyl-2-methyl-5-methoxyindole-3-acetic acid, 1-cinnamoyl-2-methyl-5,6-methylenedioxyindole-3-acetic acid, 1-(4-fluorobenzoyl)-2-methyl-5,6-methylenedioxyindole-3-acetic acid and 1-(4-chlorobenzoyl)-2-methyl-5,6-methylenedioxyindole-3-acetic acid in combination with an analgetic compound selected from the group consisting of 3-[4-(4-fluorophenyl)-4-oxobutyl]-1,2,3,4,5,6-hexahydro-6,11-dimethyl-2,6-methano-3-benzazocin-8-ol, 1,2,3,4,5,6-hexahydro-6,11-dimethyl-3-(3-methyl-2-butenyl)-2,6-methano-3-benzazocin-8-ol, 3-cyclopropylmethyl-1,2,3,4,5,6-hexahydro-6, and 11-dimethyl-2,6-methano-3-benzazocin-8-ol.

5. The analgetic composition of claim 4, wherein the indole-3-acetic acid derivative is 1-(4-chlorobenzoyl)-2-methyl-5-methoxyindole-3-acetic acid.

6. The analgetic composition of claim 4, wherein the analgetic compound is 3-[4-(4-fluorophenyl)-4-oxobutyl]-1,2,3,4,5,6-hexahydro-6,11-dimethyl-2,6-methano-3-benzazocin-8-ol.

7. The analgetic composition according to claim 1, wherein the synergistic mixture consists of 1-(4-chlorobenzoyl)-2-methyl-5-methoxyindole-3-acetic acid and 3[4-(4-fluorophenyl)-4-oxobutyl]-1,2,3,4,5,6-hexahydro-6,11-dimethyl-2,6-methano-3-benzazocin-8-ol.

8. The analgetic composition according to claim 1, wherein the synergistic mixture consists of 1-(4-chlorobenzoyl)-2-methyl-5-methoxyindole-3-acetic acid and 1,2,3,4,5,6-hexahydro-6,11-dimethyl-3-(3-methyl-2-butenyl)-2,6-methano-3-benzazocin-8-ol.

9. The analgetic composition according to claim 1, wherin the synergistic mixture consists of 1-cinnamoyl-2-methyl-5-methoxyindole-3-acetic acid and 3-[4-(4-fluorophenyl)-4-oxobutyl]-1,2,3,4,5,6-hexahydro-6,11-dimethyl-2,6-methano-3-benzazocin-8-ol.

10. The analgetic composition according to claim 1, wherein the synergistic mixture consists of 1-piperonyloyl-2-methyl-5-methoxyindole-3-acetic acid and 3-[4-(4-fluorophenyl)-4-oxobutyl]-1,2,3,4,5,6-hexahydro-6,11-dimethyl-2,6-methano-3-benzazocin-8-ol.

11. The analgetic composition according to claim 1, wherein the synergistic mixture consists of 1-cinnamoyl-2-methyl-5,6-methylenedioxyindole-3-acetic acid and 3-[4-(4-fluorophenyl)-4-oxobutyl]-1,2,3,4,5,6-hexahydro-6,11-dimethyl-2,6-methano-3-benzazocin-8-ol.

12. The analgetic composition according to claim 1, wherein said composition contains 0.05 to 90% by weight of the synergistic mixture as an active ingredients.

13. The analgetic composition according to claim 1, wherein the form of the composition is tablets, capsules, solutions, suppositories, powders or suspensions.

14. The analgetic composition according to claim 13, wherein the form of the composition is tablets, capsules or suppositories.

15. A method of obtaining improved analgesia which comprises administering to a patient a composition containing, as an active ingredient, a therapeutically effective amount of a synergistic mixture of an indole-3-acetic acid derivative of the formula,

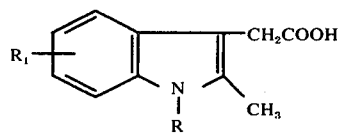

wherein R is a halobenzoyl, piperonyloyl or cinnamoyl group and $R_1$ is a 5-methoxy or 5,6-methylenedioxy group; and an analgetic compound selected from the group consisting of a compound of the formula,

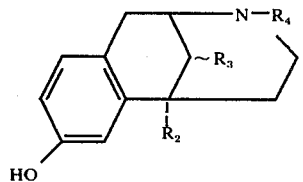

wherein $R_2$ and $R_3$ are each a $C_1 - C_3$ alkyl group and $R_4$ is a 4-(4-fluorophenyl)-4-oxobutyl, cyclopropylmethyl or 3-methyl-2-butenyl group, wherein the weight ratio of said indole-3-acetic acid and said analgetic compound is from 3:97 to 90:10.

16. The method according to claim 15 wherein the weight ratio is from 10 : 90 to 75 : 25.

17. The method according to claim 15 wherein the weight ratio is from 25:75 to 65:35.

18. The method according to claim 15, wherein the synergistic mixture contains an indole-3-acetic acid derivative selected from the group consisting of 1-(4-chlorobenzoyl)-2-methyl-5-methoxyindole-3-acetic acid, 1-cinnamoyl-2-methyl-5-methoxyindole-3-acetic acid, 1-piperonyloyl-2-methyl-5-methoxyindole-3-acetic acid, 1-cinnamoyl-2-methyl-5,6-methylendioxyindole-3-acetic acid, 1-(4-fluorobenzoyl)-2-methyl-5,6-methylendioxyindole-3-acetic acid and 1-(4-chlorobenzoyl)-2-methyl-5,6-methylendioxyindole-3-acetic acid in combination with an analgetic compound selected from the group consisting of 3-[4-(4-fluorophenyl)-4-oxobutyl]-1,2,3,4,5,6-hexahydro-6,11-dimethyl-2,6-methano-3-benzazocin-8-ol, 1,2,3,4,5,6-hexahydro-6,11-dimethyl3-(3-methyl-2-butenyl)-2,6-methano-3benzazocin-8-ol, and 3-cyclopropylmethyl-1,2,3,4,5,6-hexahydro-6,11-dimethyl2,6-methano-3-benzazocin-8-ol.

19. The method according to claim 18, wherein the indole-3-acetic acid derivative is 1-(4-chlorobenzoyl)-2-methyl-5-methoxyindole-3-acetic acid.

20. The method according to claim 18, wherein the analgetic compound is 3-(4-(4-fluorophenyl)-4-oxobutyl)-1,2,3,4,5,6-hexahydro-6,11-dimethyl-2,6-methano-3-benzazocin-8-ol.

21. The method according to claim 15, wherein the synergistic mixture consists of 1-(4-chlorobenzoyl)-2-methyl-5-methoxyindole-3-acetic acid and 3-[4-(4-fluorophenyl)-4-oxobutyl]-1,2,3,4,5,6-hexahydro-6,11-dimethyl-2,6-methano-3-benzazocin-8-ol.

22. The method according to claim 15, wherein the synergistic mixture consists of 1-(4-chlorobenzoyl)-2-methyl-5-methoxyindole-3-acetic acid and 1,2,3,4,5,6-hexahydro-6,11-dimethyl-3-(3-methyl-2-butenyl)-2,6-methano-3-benzazocin-8-ol.

23. The method according to claim 15, wherein the synergistic mixture consists of 1-cinnamoyl-2-methyl-5-methoxyindole-3-acetic acid and 3-[4-(4-fluorophenyl)-4-oxobutyl]-1,2,3,4,5,6,-hexahydro-6,11-dimethyl-2,6-methano-3-benzazocin-8-ol.

24. The method according to claim 15, wherein the synergistic mixture consist of 1-piperonyloyl-2-methyl-5-methoxyindole-3-acetic acid and 3-[4(4-fluorophenyl)-4-oxobutyl]-1,2,3,4,5,6-hexahydro-6,11-dimethyl-2,6-methano-3-benzazocin-8-ol.

25. The method according to claim 15, wherein the synergistic mixture consists of 1-cinnamoyl-2-methyl-5,6-methylenedioxyindole-3-acetic acid and 3-[4-(4-fluorophenyl)-4-oxobutyl]-1,2,3,4,5,6-hexahydro6,11-dimethyl-2,6-methano-3-benzazocin-8-ol.

26. The method according to claim 15, wherein said composition contains 0.05 to 90% by weight of the synergistic mixture as an active ingredients.

27. The method according to claim 15, wherein the form of the composition is tablets, capsules, solutions, suppositories, powders or suspensions.

28. The method according to claim 15, wherein the form of the composition is tablets, capsules or suppositories.

* * * * *